(12) United States Patent
Caiafa et al.

(10) Patent No.: US 10,968,423 B2
(45) Date of Patent: Apr. 6, 2021

(54) SYSTEM AND METHOD FOR ELECTRIC PULSE BASED ACTIVATION OF BIOLOGICAL SAMPLES

(71) Applicant: General Electric Company, Schenectady, NY (US)

(72) Inventors: Antonio Caiafa, Albany, NY (US); Vasile Bogdan Neculaes, Niskayuna, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 359 days.

(21) Appl. No.: 15/905,463

(22) Filed: Feb. 26, 2018

(65) Prior Publication Data

US 2019/0264160 A1   Aug. 29, 2019

(51) Int. Cl.
| | |
|---|---|
| C12M 1/42 | (2006.01) |
| C12M 1/00 | (2006.01) |
| C12M 1/36 | (2006.01) |
| C12M 3/00 | (2006.01) |
| C12N 13/00 | (2006.01) |
| A61B 5/15 | (2006.01) |
| G01N 35/02 | (2006.01) |
| G01N 33/487 | (2006.01) |
| A61K 35/00 | (2006.01) |
| G01N 33/49 | (2006.01) |

(52) U.S. Cl.
CPC ....... *C12M 35/02* (2013.01); *A61B 5/150343* (2013.01); *A61B 5/150755* (2013.01); *C12M 23/42* (2013.01); *C12M 29/12* (2013.01); *C12M 41/48* (2013.01); *C12N 13/00* (2013.01); *G01N 33/48707* (2013.01); *G01N 35/025* (2013.01); *G01N 35/026* (2013.01); *A61K 35/00* (2013.01); *G01N 33/49* (2013.01)

(58) Field of Classification Search
CPC .................................................. G01N 35/026
See application file for complete search history.

(56) References Cited

U.S. PATENT DOCUMENTS

| | | | |
|---|---|---|---|
| 5,591,403 A | 1/1997 | Gavin et al. | |
| 7,053,063 B2 | 5/2006 | Rubinsky et al. | |
| 7,750,605 B2 | 7/2010 | Ragsdale | |
| 7,923,238 B2 | 4/2011 | Ragsdale | |

(Continued)

OTHER PUBLICATIONS

Xiao, S., et al.; "Pulsed Power for Wood Healing", IEEE International Power Modulators and High Voltage Conference, May 2008, pp. 69-72.

(Continued)

*Primary Examiner* — Matthew D Krcha
(74) *Attorney, Agent, or Firm* — Fletcher Yoder, P.C.

(57) ABSTRACT

Disclosed herein are multi-cuvette cartridges, flow cells, and electrical pulse systems for treatment of large volumes of biological samples with pulsed electric fields. The multi-cuvette cartridges systems may include mechanical motors for automatic positioning and alignment between the cuvettes and the electrodes of the electrical pulse systems. The flow cell systems may include fluidic systems, such as pumps, nozzles and valves, which may operate in coordination with the electrical systems for efficient exposition of biological samples. Embodiments having flow cell systems that allow "on-demand" production of activated sample are also disclosed.

9 Claims, 8 Drawing Sheets

(56) References Cited

U.S. PATENT DOCUMENTS

| | | | |
|---|---|---|---|
| 8,173,416 B2 | 5/2012 | Muller-Hartmann et al. | |
| 8,222,909 B2 | 7/2012 | Ragsdale | |
| 9,011,929 B2 | 4/2015 | Park et al. | |
| 9,708,597 B2 | 7/2017 | Caiafa et al. | |
| 2007/0065945 A1* | 3/2007 | sigrist | G01N 35/1011 436/43 |
| 2009/0023131 A1 | 1/2009 | Muller-Hartmann et al. | |
| 2009/0120769 A1* | 5/2009 | Rousseau | G01N 35/04 198/844.1 |
| 2011/0318319 A1 | 12/2011 | Hargrave et al. | |
| 2014/0090957 A1* | 4/2014 | Yamauchi | B65G 47/52 198/418.5 |
| 2014/0106430 A1 | 4/2014 | Hargrave et al. | |
| 2014/0363412 A1* | 12/2014 | Neculaes | C12N 13/00 424/93.72 |
| 2015/0004717 A1* | 1/2015 | McDevitt | G01N 35/1002 436/501 |
| 2015/0202264 A1 | 7/2015 | Neculaes et al. | |
| 2016/0289664 A1 | 10/2016 | Neculaes et al. | |
| 2017/0191052 A1 | 7/2017 | Neculaes et al. | |
| 2017/0314009 A1 | 11/2017 | Caiafa et al. | |

OTHER PUBLICATIONS

Khine, Michelle, et al.; "Single-cell electroporation arrays with real-time monitoring and feedback control," Lab Chip 2007, 7, 457-462.

JP Application No. 2016-545972; Office Action dated Dec. 20, 2018; 8 pages, including translation.

RU Application No. 2016126427; Office Action, dated Oct. 26, 2018; 6 pages.

TW Application No. 104100402; Office Action, 7 pages.

Xiao, S., et al.; "Pulsed Power for Wound Healing", Frank Reidy Research Center for Bioelectrics, Old Dominion University, 2008, pp. 1-4.

Zhang, Jue, et al.; "Nanosecond Pulse Electric Field (nanopulse): A Novel Non-Ligand Agonist for Platelet Activation", Archives of Biochemistry and Biophysics 471 (2008), pp. 240-248.

Zhou, Lan, et al.; "Platelet Aggregation Testing in Platelet-Rich Plasma", American Society for Clinical Pathology, pp. 172-183, 2005.

Meng, Shiyun, et al.; "Electrical Stimulation in Tissue Regeneration," Applied Biomedical Engineering, Dr. Gaetano Gargiulo (Ed.), ISBN: 978-953-307-256-2, InTech, Available from: http://www.intechopen.com/books/applied-biomedical-engineering/electrical-stimulation-in-tissueregeneration, 2011.

Caiafa, Antonio, et al.; "Compact Solid State Pulsed Power Architecture for Biomedical Workflows: Modular Topology, Programmable Pulse Output and Experimental Validation on Ex Vivo Platelet Activation", Power Modulator and High Voltage Conference, Jun. 1-5, 2014.

Paniccia, Rita, et al.; "Platelet Function Tests: A Comparative Review", Vascular Health Risk and Management, pp. 133-148, 2015.

* cited by examiner

SYSTEM AND METHOD FOR ELECTRIC PULSE BASED ACTIVATION OF BIOLOGICAL SAMPLES

BACKGROUND

The subject matter disclosed herein relates to electric pulse based activation of biological samples using methods and systems that use automated cartridges devices or flow cell devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it may be understood that these statements are to be read in this light, and not as admissions of prior art.

Use of activated platelet rich plasma (also called "activated platelets") is an emerging therapeutic approach that may be employed in clinic or other health care facility. For example, activated platelet rich plasma can be used to produce activated platelet compounds for therapeutic use. Therapeutic uses of activated platelet compounds include promoting wound healing (such as after surgery) and hemostasis. In particular, interest in the use of activated platelet therapy as a wound healing treatment exists for many types of injuries and conditions such as nerve injuries, tendinitis, osteoarthritis, cardiac muscle injury, and bone repair and regeneration. The derivation of the activated platelet products used on a patient may be autologous, meaning that the activated platelet compound is derived from the patient's own tissues and/or fluids. Thus, a blood sample from the patient may be used to derive the activated platelet compound used to treat the patient.

By way of example, a doctor may draw blood from a patient and platelets in the blood sample may be activated. Upon activation, the platelets within the blood release growth factor and proteins that facilitate and promote the wound healing cascade. The clinical workflow, thus, may involve drawing blood from the patient, centrifuging the blood to separate out the platelets, and performing an ex vivo platelet activation. Activation of platelets may involve exposing the biological sample to pulsed electric fields. The activated platelets or platelet gel may then be applied to the wound or other treatment region.

Due to spatial and geometric constraints of the existing apparatuses capable of applying electrical fields to biological samples, the volumes of samples that can be activated using pulsed electric fields may be limited by the volume of a cuvette, which is usually between 10 µl and 1 ml. As a result, a clinician may find substantial challenges when employing electric pulsed fields for platelet activation-based therapies in which the amount of samples are substantially larger than the cuvette volume. Manual repetition of the process to produce larger amounts of activated-platelet compounds often results in inconsistent results across samples, reducing the efficacy of the therapy. Moreover, existing devices that are used for application of electric fields to biological samples may not be appropriate for use in clinical settings. Existing pulse generating systems may not be appropriately set for receiving blood or platelet rich plasma samples, and may lack pre-configured protocols for platelet activation. These systems may also lack safeguards to preserve sterility of the product.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, an electric pulse generation system is described. The electric pulse generation system includes a sample holder having a pair of sample loader electrodes adjacent to a cartridge rail. The cartridge rail can hold a cuvette cartridge having multiple cuvettes, and each cuvette has a respective pair of electrodes. The system may also include a mechanical motor that can move the cuvette cartridge along the cartridge rail, a pulse generating circuitry electrically coupled to the pair of sample loader electrodes adjacent to the cartridge rail, and a controller that controls the pulse generating circuitry and the mechanical motor. The controller may, among other things, operate the mechanical motor to position the cuvette cartridge such that the respective pair of electrodes of a target cuvette in the cartridge is aligned with the pair of sample loader electrodes, and operate the pulse generating circuitry to cause a pulse electric field in the target cuvette.

In another embodiment, another electric pulse generation system is described. This electric pulse generating system includes a sample loader having first and second reservoirs, which are connected by a channel, and a pump that is capable of inducing flow from the first to the second reservoir through the channel. The channel includes a pair of electrodes. The system also includes pulse-generating circuitry coupled to the pair of electrodes. The system also includes a controller having processing circuitry and a memory having instructions for activating the pump to induce flow at a first flow rate, and for causing the pulse generating circuitry to generate an electrical pulse sequence between the pair of electrodes. The generated electrical pulse sequence may have at least one characteristic, such as electric field intensity, or pulse frequency, based on the flow rate.

In another embodiment, an activated platelet treatment system is described. This system includes a platelet activation circuitry, having an internal channel, a pair of electrodes coupled to the internal channel, and a pump that can induce a flow through the channel. The system also includes a collection tube and an application tube coupled to the internal channel. The collection tube may receive a blood sample (e.g., raw blood, plasma, platelet-rich plasma), and the application tube may receive an activated platelet product. The system further includes a controller that may activate the pump to induce the flow from the collection tube to the application tube through the internal channel and to generate pulsed electric fields between the pair of electrodes that activate platelets in the blood sample.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, certain features of an actual implementation may not be omitted in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," and "in one (an) embodiment."

Platelet activation and/or aggregation may be used to treat wounds in vivo and/or ex vivo. For in vivo platelet activation, inactive platelet rich plasma (PRP) is applied or injected at the site of injury and activated by naturally occurring compounds within the body, such as collagen present in the connective tissue. By contrast, in ex vivo processes, platelets in pre-processed blood samples (e.g., PRP) are activated prior to being injected in the site of the injury. Activation may take place exposing the blood, plasma, or PRP samples to a platelet-activating compound, such as thrombin, which induces the release of growth factors (e.g., platelet-derived growth factor (PDGF)). Activation may also take place by exposing the blood, plasma, or PRP samples to pulsed electric fields. For example, for ex vivo platelet activation, a doctor may draw blood from a patient and centrifuge the blood sample to produce a PRP sample. Calcium chloride ($CaCl_2$) and a platelet-activating compound, such as thrombin, may be added to the PRP sample to trigger platelet activation. These additives may be added as solution, suspension, or pure. The PRP sample may also be exposed to electric field pulses, which may be used for custom activation of platelets and/or release of growth factors by use of specific pulse sequence protocols. More specifically, in response to one or more customizable or tunable electric field pulses that may be applied, the release of various levels or amounts of growth factor may be obtained. The electric field customization may take place by adjustment of, among other things, target electric field, peak voltage, pulse width, number of pulses, pulse period, and/or pulse shape, among other parameters.

In addition to the release of growth factors, pulsed electric fields, applied alone, or in conjunction with the activating compound, may be used to control the release of other factors in an activation procedure. For example, activated platelets (or other cells in the exposed sample) may release endogenous antioxidants, reactive oxygen species, matrix metalloproteinase-2 (MMP-2) and other factors in a tunable or adjustable way in response to proper electric field pulses. The tunable or customizable activation, thus, may involve not only customized release of growth factors, but of other factors (such as those listed above), which may be relevant to the wound healing process. Generation of customized activated platelet composition using electric pulse fields is described in U.S. patent application Ser. No. 14/674,971 entitled "ACTIVATED PLATELET COMPOSITION WITH TUNABLE GROWTH FACTOR LEVEL," filed on Mar. 31, 2015, which issued as U.S. Pat. No. 9,752,120, and is incorporated by reference herein in its entirety for all purposes.

Ex vivo platelet activation, as discussed herein, involves exposing a blood sample, such as blood, plasma, PRP, or any suspension containing platelets, to electrical pulses (e.g., exposure to pulsed electric fields) to trigger platelet activation, though exposure to other types of energy are also contemplated and encompassed. The methods for ex vivo growth factor release may or may not involve chemicals additives and/or platelet activating compounds being added to the blood sample prior to electrical pulse stimulation. As discussed herein, activation may or may not involve the destruction (e.g., lysis) of cells (e.g., red blood cells) within the sample, depending on the parameters of the activation exposure. In certain embodiments electrical stimulation or activation may be applied using different electrical parameters (e.g. amplitude, voltage, electric field, energy density, current, pulse width, number of pulses, and so forth), with different parameters or combinations of parameters yielding different growth factor levels and/or different proportions of growth factors relative to one another. Such differently formulated activated compositions may be used to achieve different biological or medical effects (e.g., enhanced wound healing), and the desired effect may therefore determine the electrical pulse parameters employed in activating a given cellular composition.

The ex vivo platelet activation using electric field pulses may take place by placing a sample between conductive electrodes of a cuvette and establishing an electric pulse potential between the two conductive electrodes. The region of the sample between the conductive electrodes may be exposed to a pulsed electric field, which may lead to activation of the platelets in the region. The separation between the two electrodes, also referred to herein as electrode gap or cuvette gap, is usually limited to under 1-2 cm, due to practical considerations. As will be appreciated, for a given voltage applied between electrodes, a larger spacing between the pair of electrodes in the sample loader may be associated with a weaker pulsed electric field, defined as the ratio of the applied voltage and the cuvette gap distance. For example, to obtain a field strength of 1 kV/cm using a 1 cm wide cuvette, a 1 kV pulse may be used. By contrast, the same field strength using a hypothetical cuvette having a 10 cm cuvette gap would require a 10 kV pulse should be used, which would demand an impractically complex pulse generating system. As a result, the volume of activated sample that may be produced is limited to few milliliters (e.g., less than 1-2 ml). In therapies that may benefit from several milliliters (10-20 ml, or more) of activated platelet product, the use of electric field pulses may be cumbersome.

Embodiments described herein relate to electric field activation apparatuses that may be used to generate larger volumes of activated platelet compounds ex vivo. As detailed herein, some embodiments employ an automated method for activation of multiple cuvettes placed in a cartridge-style mechanism. Some embodiments employ "flow cells," flow channels that may have electrode surfaces used to expose blood samples to pulsed electric fields during a controlled flow between activated electrodes. Methods of operation of the systems are also discussed. While the methods and systems herein are described in the context of platelet activation in blood samples, the methods and systems described herein may be adapted for other applications in which biological material may be exposed to electric field pulses, such as in electroporation systems for insertion of nucleotides into cells, and immune cell activation for immune therapy.

Figure 1:
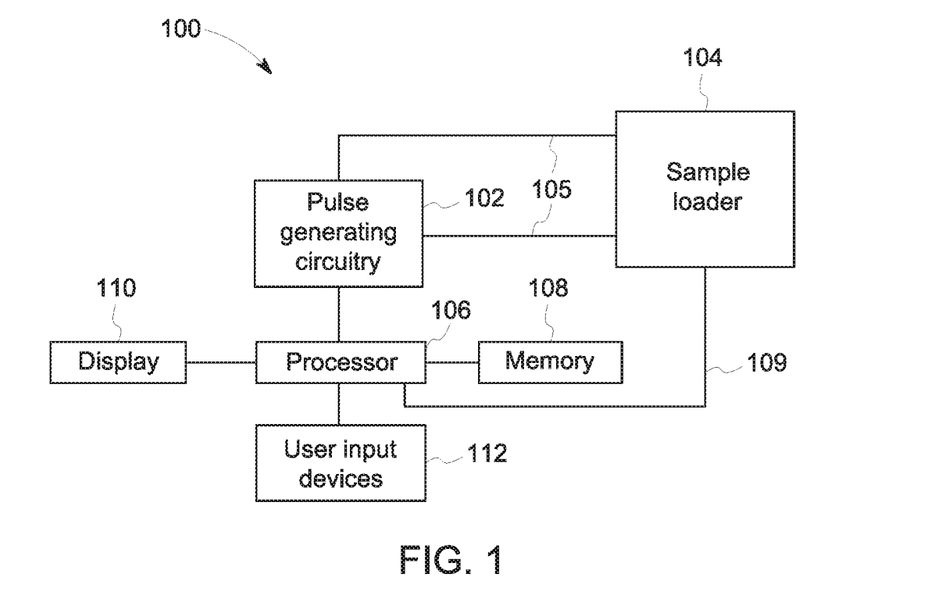
FIG. 1 is a schematic of a pulse generation system that may be used for large volume platelet activation, in accordance with an embodiment.

With the foregoing in mind, FIG. 1 shows schematically a pulse generation system 100 for large volume ex vivo platelet activation and customizable or tunable growth factor release. The system 100 includes pulse generating circuitry 102 and a sample loader 104. In the depicted embodiment, the sample loader 104 is electrically coupled to the pulse generating circuitry 102 by an electrical connection 105. As detailed below, embodiments of the sample loader 104, include, at least, a pair of electrodes coupled electrically to the electrical connection 105, and a receptacle for samples that includes a volumetric region disposed between the pair of electrodes. It should be understood that the electrical connection 105 discussed herein may be resistive, capacitive, and or inductive.

In certain embodiments, the system may include control and input circuitry and may be implemented in a dedicated housing or may be coupled to a computer or other processor-based control system. For example, the system 100 may include a processor 106 that controls the pulse generating circuitry 102. To that end, the processor 106 may cause the pulse generating circuitry 102 to electrically stimulate or activate a blood, blood component or platelet suspension placed in sample loader 104. Field strength, electrode separation distance, and other parameters related to the generated electrical pulses are factors, as discussed herein, that may be varied or adjusted to vary the growth factor levels with respect to one another during an activation procedure. Based on these factors, the processor may determine an electrical signal that the pulse generating circuitry 102 induces in the electrical connection 105.

The processor 106 may also control the mechanisms for operation of the sample loader 104 using a control signal 109, as further detailed below. For example, in the flow cells, in which the biological samples are exposed to pulsed electrical field while undergoing flow, the flow rate and the flow channel diameter may be adjustable factors, which may be used to vary the growth factor levels in the activated platelet compounds. As such, the processor may coordinate the pulse provided in electrical connection 105 with the control signals provided via control signal 109.

Additional components of the system 100 may include a memory 108 that stores instructions executed by the processor 106. Such instructions may include protocols and/or parameters for generating electric pulses using the pulse generating circuitry 102, as well as instructions for operation of the sample loader 104 using control signal 109. The processor 106 may include, for example, general-purpose single- or multi-chip microprocessors. In addition, the processor 106 may be any conventional special purpose processor, such as an application-specific processor or circuitry. The memory 108 may be any suitable non-transitory computer-readable medium such as a random access memory, mass storage device, a solid-state memory device, or removable memory.

In addition, a display 110 may provide indications to an operator related to the operation of the system 100. The system 100 may also include a user input device 112 (e.g., a keyboard, mouse, touchscreen, trackball, hand held device such as PDA or smart phone or any combination thereof) to operate the pulse generating circuitry 102 and the sample loader 104, selecting or specifying appropriate electric pulse parameters, number of samples, volume of a sample, diameter of a flow cell, electrode gap dimensions, flow pressure, and other such parameters for operation of system 100. Moreover, the user may employ user input device 112 to select a pre-configured pulse profile from among a number of such profiles (such as profiles each corresponding to different stages of wound healing), which may be stored in the memory. The user input device 112 may also be a dedicated control system that allows "on-demand" interaction. Examples of such systems are discussed with respect to the "on-demand" embodiments illustrated in FIGS. 9-11.

By way of example, in one embodiment, a pulse generated by the system 10 may have a duration from about 1 nanosecond to about 100 microseconds, and an electric field strength from about 0.1 kV/cm to about 350 kV/cm, depending on the application. The activation protocol may also employ pulse sequences (i.e., a series of electric pulses), and each pulse within a pulse sequence may induce electric fields with different strengths and/or durations. While the pulses generated by the system 100 typically have an electric field strength of 0.1 kV/cm or greater, the pulses typically will not exceed the breakdown field of the suspension which includes the cells. Moreover, in some embodiments, the pulse generation system 100 may include sensing functionality. To that end, the pulse generation circuitry 102 may expose a sample in the sample loader 104 to a sensing signal. The sensing signal (e.g., a voltage) may be an electric pulse that causes an electric field strength smaller than the electric fields used for cellular activation, and the response to the sensing signal (e.g., the electrical current in response to the voltage) may be measured in the pulse generating circuitry 102. In the embodiments described herein, electrodes may be metallic electrodes (e.g., including stainless steel, tungsten, platinum, iridium, platinum-iridium alloys, iridium oxide, titanium nitride, etc.), salt bridge electrodes, carbon nanotube electrodes, conductive polymers (e.g., conductive polymer films).

Figure 2:
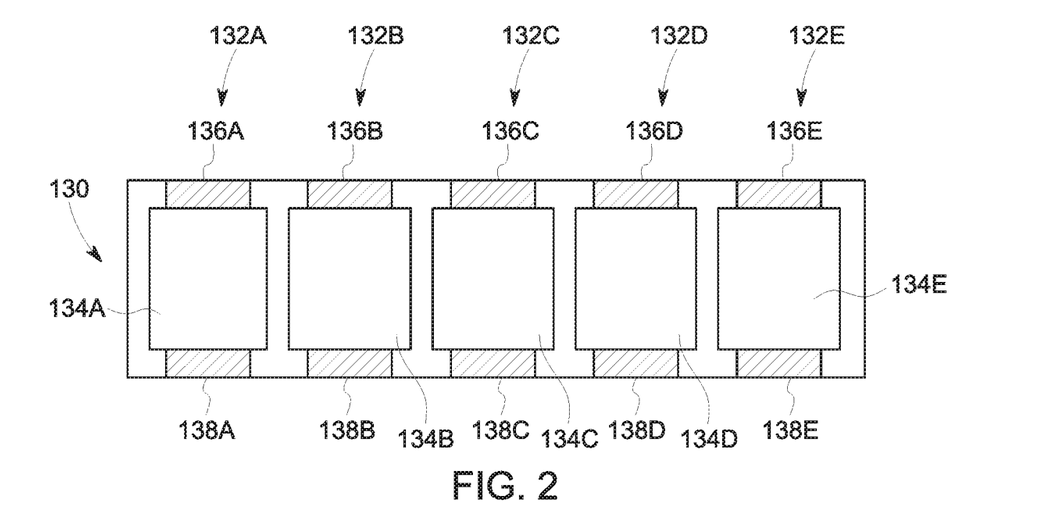
FIG. 2 is a schematic of a linear cuvette cartridge that may be used for large volume platelet activation of biological samples, in accordance with an embodiment.

FIG. 2 illustrates a cuvette cartridge 130 that may be used to increase the volume of activated product. The cuvette cartridge 130 may be a linear cuvette cartridge. The illustrated cuvette cartridge 130 includes 5 sample receptacles 132A, 132B, 132C, 132D, and 132E. Each sample receptacle has a respective inner volume 134A, 134B, 134C, 134D, and 134E, for placement of the sample. Each inner volume may be disposed between two electrodes. In the example, inner volume 134A is disposed between electrodes 136A and 138A, inner volume 134B is disposed between electrodes 136B and 138B, inner volume 134C is disposed between electrodes 136C and 138C, inner volume 134D is disposed between electrodes 136D and 138D, and inner volume 134E is disposed between electrodes 136E and 138E. In the illustrated embodiment, the cuvette cartridge 130 is constructed in a monolithic manner. A cuvette cartridge 130 may also be constructed in a modular embodiment by having a frame in which cuvettes may be placed. For example, receptacles 132A, 132B, 132C, 132D, and 132E may be a structural support (e.g., a cuvette receptacle, a frame that can receive cuvettes) that is configured to receive individual cuvettes. The individual cuvettes may have, each, respective inner volumes 134A, 134B, 134C, 134D, and 134E, and a respective pair of electrodes 136A and 138A, 136B and 138B, 136C and 138C, 136D and 138D, 136E and 138E. While the example described herein relates to a 5-cuvette cartridge, the present description is not limited to linear cuvette cartridge embodiments having 5 cuvettes and the number of cuvettes may be increased and/or decreased with adjustments to the linear cuvette cartridge design.

Figure 3:
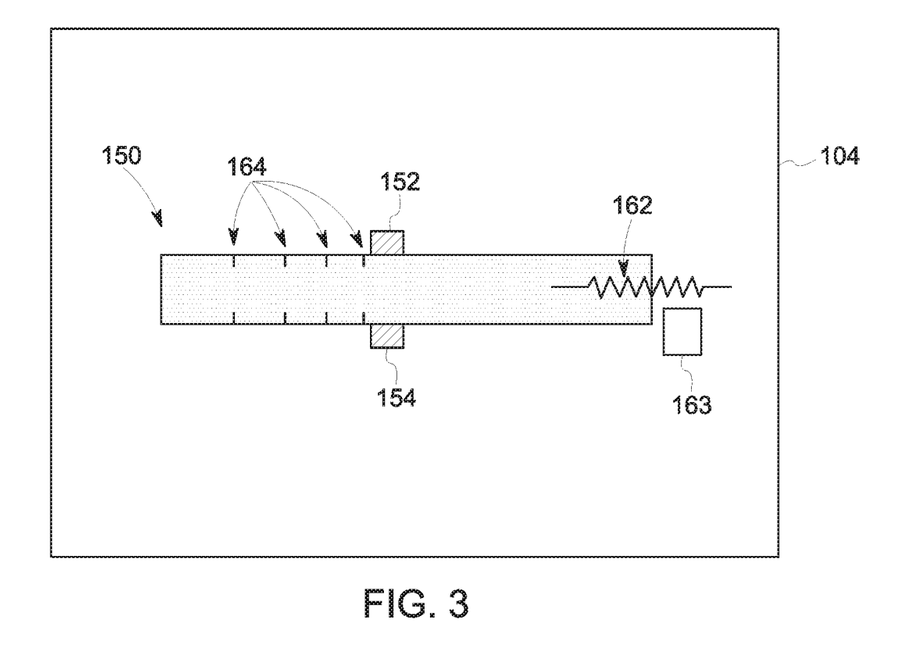
FIG. 3 is a schematic of a sample loader that may be used with the linear cuvette cartridge of FIG. 2, in accordance with an embodiment.

Cartridge 130 of FIG. 2 may be used in combination with the sample loader 104 illustrated in FIG. 3. The illustrated sample loader 104 is a linear cartridge sample loader. The sample loader 104 may have a cartridge rail 150, configured to receive the cuvette cartridge 130. Generally, the cartridge rail 150 may be at least twice as long as the cuvette cartridge 130. Sample loader 104 may also have electrodes 152 and 154 (e.g., sample loader electrodes), which may be coupled to the electrical connection 105, as illustrated in FIG. 1. Moreover, the cartridge rail 150 may have a mechanical lever 162. The mechanical lever 162 may be coupled to a controllable motor 163, which may cause the mechanical lever 162 to move. The mechanical lever 162 may be used to move the cuvette cartridge 130 during the process, as detailed in FIGS. 4A, 4B, 4C, 4D, and 4E. The mechanical lever 162, thus, may be used to move the cuvette cartridge 130 along the cartridge rail 150 and to align the electrodes of the cuvette cartridge 130 (e.g., electrodes 136A-E and electrodes 138A-E) with electrodes 152 and 154.

As illustrated in FIG. 3, the mechanical lever 162 may be implemented using a "spring" system with mechanical stops 164. In such system, a mechanical stop 164 holding the cuvette cartridge 130 in place may be dislodged such that it does not impede movement of the cuvette cartridge. In a coordinated action, the mechanical lever 162 may receive a motive force from the motor 163 to move the cuvette cartridge to the next mechanical stop 164. The mechanical lever 162 may also be implemented using a "screw" system. In such system, the motor 163 is coupled to the mechanical lever 162 through a screw coupling, and the movement of the mechanical lever 162 may be controlled by the number of turns of the motor 163. Other methods capable of inducing a controlled movement of the mechanical lever 162 and of the cuvette cartridge 130 may also be used.

Figure 4A:
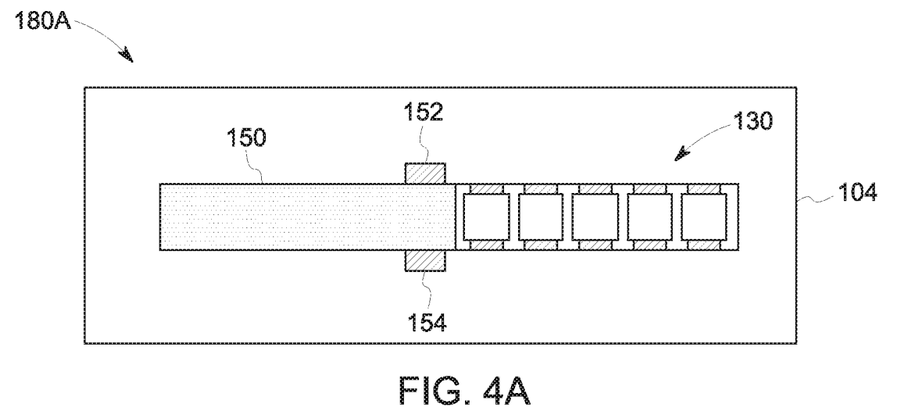
FIG. 4A is the first schematic of a series of schematics to illustrate the operation of the sample loader of FIG. 3, in accordance with an embodiment.
Figure 4B:
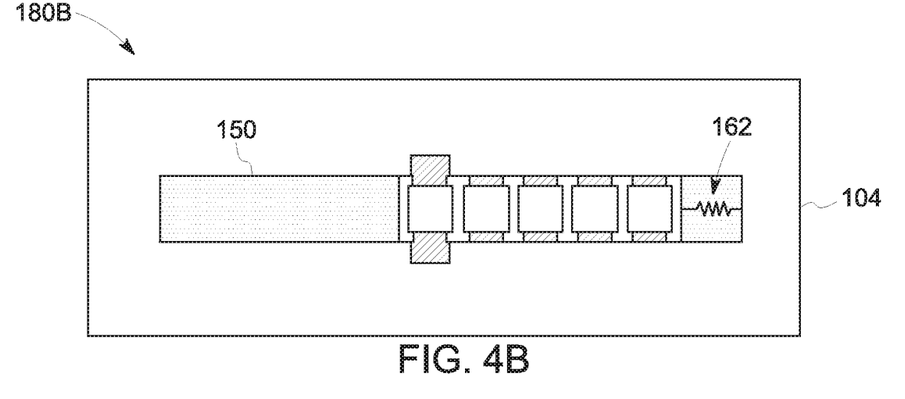
FIG. 4B is the second schematic in the series of schematics to illustrate the operation of the sample loader of FIG. 3, in accordance with an embodiment.

The schematic illustrations in FIGS. 4A, 4B, 4C, 4D, and 4E illustrate the operation of the linear cartridge system illustrated in FIGS. 2 and 3. The first schematic illustration 180A in FIG. 4A illustrates the linear cartridge system at the beginning of operation. The cuvette cartridge 130 may be placed at an end of the cartridge rail 150. At this initial stage, no cuvette is electrically coupled to the electrodes 152 and 154. After initialization, the cuvette cartridge 130 may be moved to prepare the first cuvette for electric field exposure, as illustrated in the second schematic illustration 180B in FIG. 4B. The mechanical lever 162 moved the cuvette cartridge 130 such that the electrodes of the first cuvette are aligned with electrodes 152 and 154. At this position, the pulse generating circuitry (e.g., pulse generating circuitry 102 of FIG. 1) may induce a pulsed electric field in the first cuvette, to activate the blood sample or the PRP sample disposed therein.

Figure 4C:
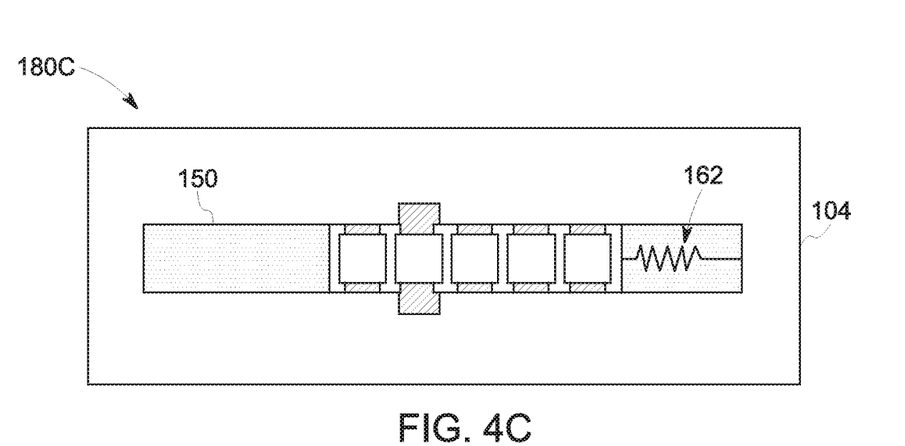
FIG. 4C is the third schematic in the series of schematics to illustrate the operation of the sample loader of FIG. 3, in accordance with an embodiment.
Figure 4D:
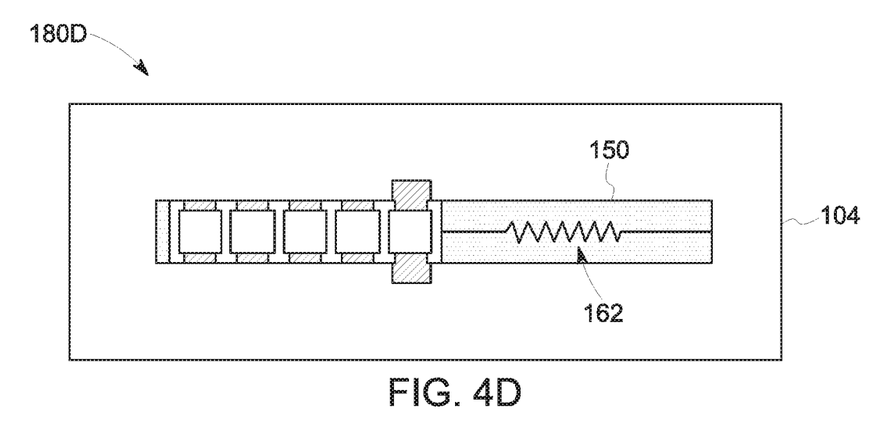
FIG. 4D is the fourth schematic in the series of schematics to illustrate the operation of the sample loader of FIG. 3, in accordance with an embodiment.
Figure 4E:
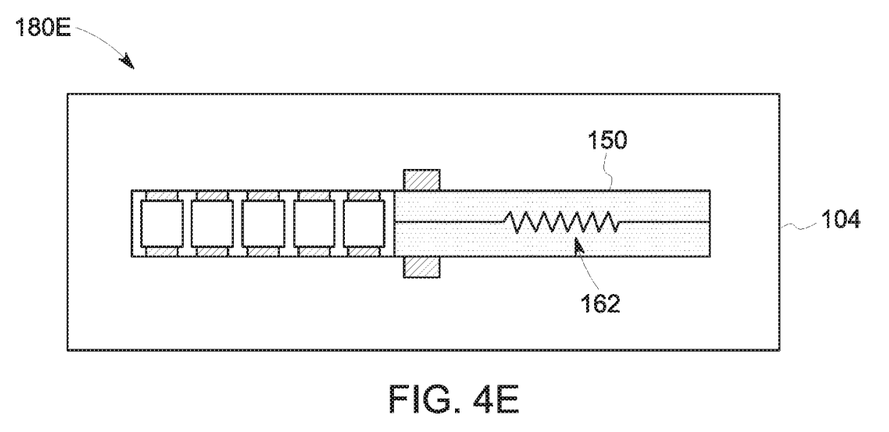
FIG. 4E is the fifth schematic in the series of schematics to illustrate the operation of the sample loader of FIG. 3, in accordance with an embodiment.

Following the first activation, the mechanical lever 162 may move the cuvette cartridge 130 to the position illustrated in the third schematic illustration 180C in FIG. 4C. In the position indicated in FIG. 4C, the second cuvette of the sequence may have its electrodes aligned with electrodes 152 and 154. At this moment, the pulse generating circuitry may induce a pulsed electric field in the second cuvette, to activate the blood sample or the PRP sample disposed therein. The process including movement of the cuvette cartridge 130 and electrical pulsing via electrodes 152 and 154 may be repeated until the last cuvette of the cuvette cartridge 130 is subjected to the pulsed electric field. This final state is illustrated in the fourth schematic illustration

180D in FIG. 4D. This position may be reached following activation of samples in the third and fourth cuvettes (not depicted in this example for clarity). In the position illustrated in the fourth schematic illustration 180D, an activating pulse may be provided via electrodes 152 and 154. Following the activation of the last sample, the mechanical lever may move the cuvette cartridge 130 to a final position, illustrated in the fifth schematic illustration 180E in FIG. 4E. At this point, the activated platelet compound may be ready for collection and use in therapy.

The cuvette cartridge 130 and the cartridge rail 150 may, in coordination with the pulse generating circuitry 102, be used to produce more complex activation protocols. For example, mechanical lever 162 may allow movement of the cuvette cartridge 130 in the opposite direction as the one illustrated in FIGS. 4A-D. Movement of the cuvette cartridge 130 in the opposite direction as the one illustrated in FIGS. 4A-D may also be obtained by a second mechanical lever operationally coupled to the cartridge rail 150. In such system, the protocol used for platelet activation may involve multiple applications of a pulsed electric field pulses separated by a "rest period." For example, a protocol stored in the memory of system 100 may have a first pulse instruction, in which each cuvette of the cuvette cartridge 130 receive a first pulse sequence in the manner discussed above, a cartridge return instruction, in which the cuvette cartridge is automatically returned to the starting point (i.e., the cuvette cartridge 130 is returned from the position illustrated in FIG. 4E to the position illustrated in FIG. 4A), and a second pulse instruction, in which each cuvette of the cuvette cartridge 130 receive a second pulse sequence. This type of protocol may be used to include "rest periods" in the activation protocol of large volumes of blood samples, without substantial additional delays. In fact, in a protocol that includes a 1-minute rest period between two pulse sequences, the cartridge return instruction may add a little over 1 minute to the protocol, whereas a naive solution (e.g., apply the first and the second pulse sequence to the first cuvette in the cuvette cartridge rail before applying the first and the second pulse sequence to the second cuvette in the cuvette cartridge rail) may add, at least, 1 minute per cuvette in the cuvette cartridge.

Figure 5:
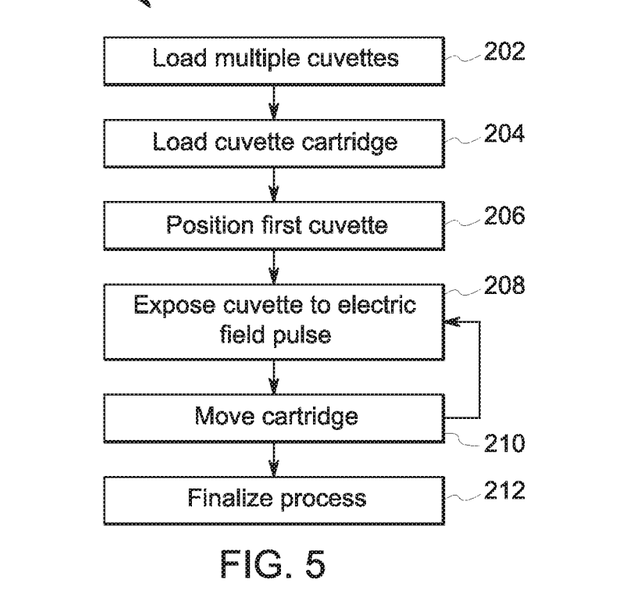
FIG. 5 is a flowchart for a method to operate cartridge-based cuvette loading systems for platelet activation, in accordance with an embodiment.

The use of cuvette cartridges for large volume processing is further illustrated in the method 200 illustrated by the flowchart in FIG. 5. In box 202, a user may insert the whole blood or PRP samples into the multiple cuvettes of the cuvette cartridge. The cuvettes may be loaded manually or using an automatic system. In box 204, the cuvettes may be inserted into the cuvette cartridges, in modular embodiments (e.g., systems in which the cuvette cartridge is a structural support to receive cuvettes, as described above). It should be noted that, in monolithically built cuvette cartridges, the processes described by box 202 and 204 may have some overlap. In box 206, the user may place the cuvette cartridge into the cartridge rail, in its initial position. A non-limiting example of an initial position was shown in FIG. 4A above. After placing the cuvette cartridge in the initial position, the user may initiate the process in system 100 by running a protocol, which may be stored in the memory.

To activate the samples in each cuvette, the method 200 may iterate multiple times through the processes represented by box 208 and 210. In box 208, the cuvette of the cuvette cartridge that is aligned with the electrodes of the sample loader 104 may be exposed to the electric field pulses. In box 210, the sample loader 104 may move the cuvette cartridge to align another cuvette with the electrodes of the sample loader 104. Examples of the described iterations were discussed with respect to FIGS. 4A-E. Note further that, as discussed above, the process represented by box 210 may also move the cartridge to allow cuvettes to receive multiple pulse sequences to implement, for example, protocols that include "rest" periods. At the end of the process, in box 212, the cuvettes in the cuvette cartridge may contain the activated platelet product, as customized by the protocol. The user may collect the product from the cuvettes and use it for therapeutic purposes.

Figure 6:
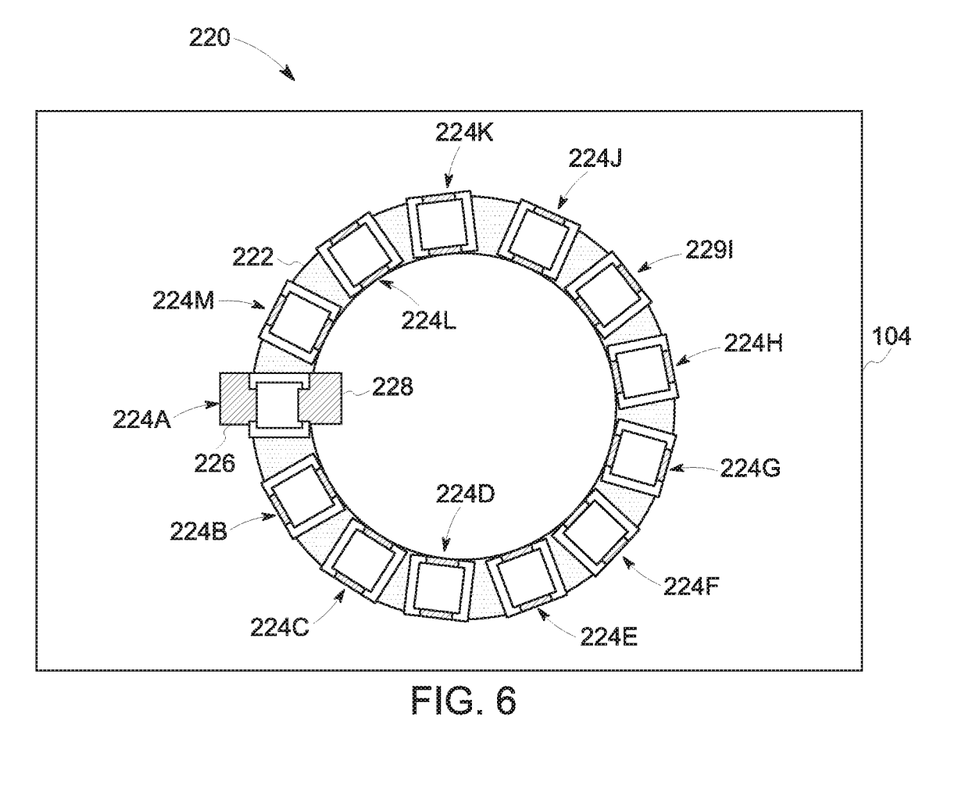
FIG. 6 is a schematic of a circular sample loader and a circular cuvette cartridge that may be used for large volume activation of biological samples, in accordance with an embodiment.

Method 200, discussed above, may also be used with a sample loader 104 having other geometries, such as a non-linear geometry. Schematic diagram 220 illustrates a sample loader 104 having a circular rail 222. The illustrated circular rail 222, has 13 cuvettes 224A, 224B, 224C, 224D, 224E, 224F, 224G, 224H, 224I, 224J, 224K, 224L, and 224M. As illustrated, each cuvette has a pair of electrodes that, when aligned with electrodes 226 and 228 of the sample loader 104, electrically couple to the pulse generating circuitry 102. In the system with a circular rail 222, the movement associated with box 210 of FIG. 5 may be a circular rotation (e.g., an angular rotation) of the circular rail 222. While the example described herein relates to a 13-cuvette cartridge, the present description is not limited to circular cuvette cartridge embodiments having 13 cuvettes and the number of cuvettes may be increased and/or decreased with adjustments to the circular rail 222.

As noted above, the exposure of multiple cuvettes to electric pulses in an automatic system 100 may be used to process large volumes. Large volumes may also be exposed by using a flow cell 241 with electrodes, such as the one illustrated in diagram 240 of FIG. 7. The flow cell 241 may include two sample reservoirs 242 and 244. The samples may flow between sample reservoirs 242 and 244 through the connecting channel 245. Reservoirs 242 and 244 may be implemented as flexible plastic bags that may be non-conductive (e.g., non-electrically conductive) and/or biocompatible, such as polypropylene and/or polyethylene bags. In embodiments employing flexible plastic bags, the flow between reservoirs 242 and 244 may be induced by means of a compression system (e.g., a pressure pump) of the sample loader 104. The mechanism for induction of flow using a compression system is described in further detail with respect to FIGS. 8A and 8B below. Flow between the reservoirs 242 and 244 through the connecting channel 245 may be induced using other mechanisms for sterile flow between systems, for example, a peristaltic pump coupled to channel 245.

Figure 7:
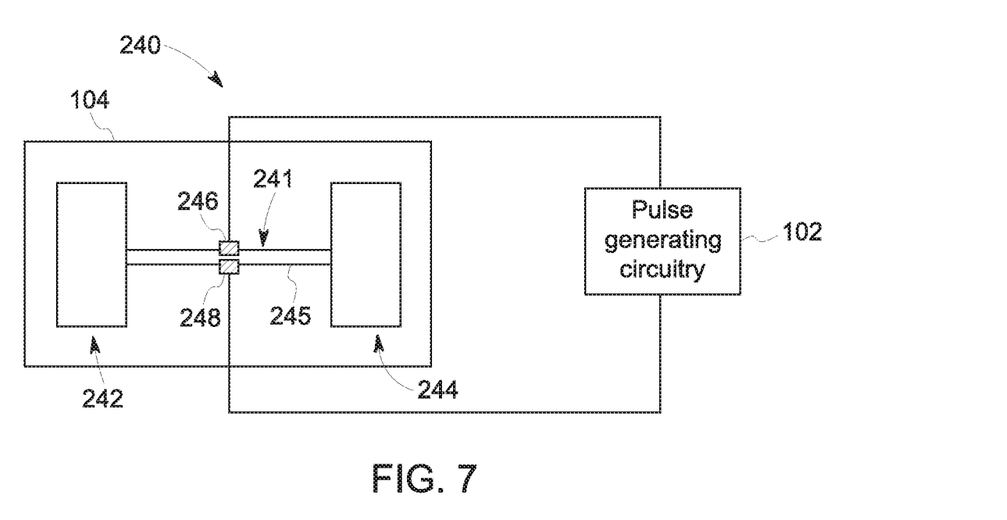
FIG. 7 is a schematic of a flow-based sample loader that may be used for large volume activation of biological samples, in accordance with an embodiment.

The channel 245 may be constructed to include a pair of electrodes 246 and 248. The arrangement between the pair of electrodes 246 and 248 and the channel 245 is such that, when an electric potential between electrodes 246 and 248 is provided, the sample volume disposed in the region between the pair of electrodes is subjected to a pulsed electric field. Electrodes 246 and 248 may have surface in the interior of the channel 245 such that the sample flowing through the channel may come into contact with the electrodes 246 and 248, to close the electrical circuit that allows the generation of the pulsed electric fields.

The flow cell 241 allows the electrode gap, i.e., the distance between the pair of electrodes 246 and 248, to be independent from the processed sample volume, which may be the volume of the reservoir 242 and 244. For example, a flow cell having an electrode gap between 1 mm-1 cm may process, for example, volumes ranging from 500 µl to 100 ml, and may be scaled up to several liters with appropriate design. This independence between the sample volume and the electrode gap may allow reduction in the overall voltages provided by the pulse generating circuitry 102. In fact, the electrode gap may be reduced without sacrificing the sample volume of activated product generated. For example, to produce an electric field of 1 kV/cm using a flow cell 241 with an electrode gap of 10 mm, pulse-generating circuitry 102 may use 100V electric pulses between electrodes 246 and 248. By contrast, to produce the same 1 kV/cm electric field using a traditional 1 cm cuvette, the pulse-generating circuitry 102 may be dimensioned to output 1 kV, which would require more complex power generating circuitry.

Figure 8A:
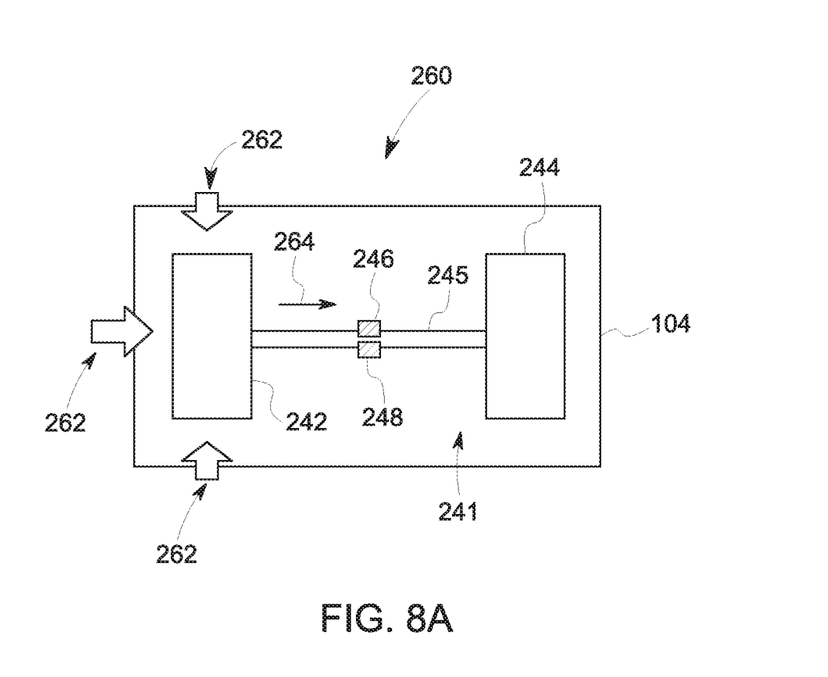
FIG. 8A is the first schematic of a series of schematics illustrating the operation of the sample loader of FIG. 7, in accordance with an embodiment.
Figure 8B:
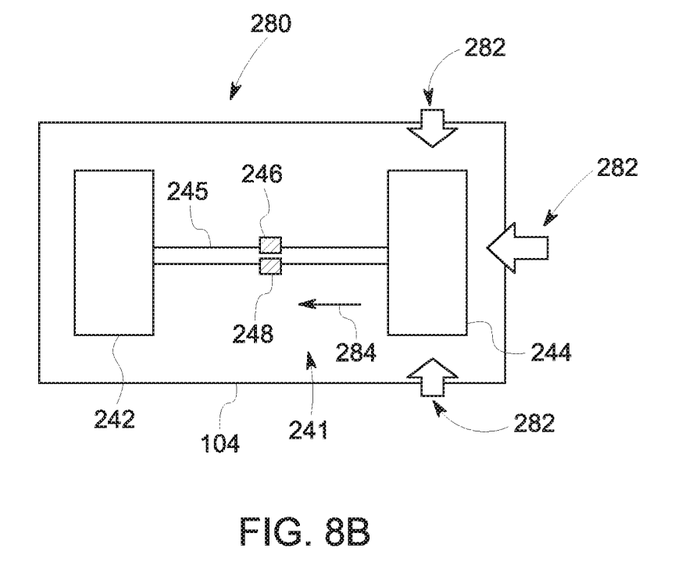
FIG. 8B is the second schematic of the series of schematics illustrating the operation of the sample loader of FIG. 7, in accordance with an embodiment.

Operation of the flow cell 241 is illustrated in FIGS. 8A and 8B. The first schematic diagram 260 in FIG. 8A illustrates a situation in which the flow cell 241 is shifting or moving the sample from a first reservoir 242 to a second reservoir 244. In this example, a pressure pump coupled to the first reservoir 242 creates a pressure 262 on the flexible walls of the reservoir 242. Such pressure induces the flow 264 that moves the sample through channel 245. While the sample is flowing through the channel 245, the pulse generating circuitry 102 generates pulsed electric fields in the volume of the sample located between electrodes 246 and 248, as the sample flows along channel 245. This process may continue until all the sample is moved from reservoir 242 to reservoir 244, as illustrated in the schematic diagram 280 in FIG. 8B. At this moment, a second pressure pump (not shown) coupled to the second reservoir 244 creates a pressure 282 on the walls of the reservoir 242 that generates a flow 284 of the sample back to reservoir 242 through channel 245. During the flow 284, the pulse generating circuitry 102 generates pulsed electric fields in the volume of the sample that is located between electrodes 246 and 248 as sample flows through along the flow path.

The application of pulsed electric fields using electrodes 246 and 248 may be applied in a continuous manner. In such a system, the pulse generating circuit 102 may generate a high frequency alternating pulse (AC) signal (positive and negative sequentially). The AC signal generated may have its frequency determined based on the flow rate of flows 264 and 284, and the length of the electrodes 246 and 248 in contact with the sample as the sample flows along the internal surface of the connecting channel 245. For example, in some embodiments a faster flow rate may lead to a higher frequency. As another example, longer electrode lengths in contact with the sample may allow use of a reduced frequency. The flow rate of flow 264 may be calculated from the pressure in the system or based on a direct measurement of the speed in the channel 245. As an example, in a flow cell 241 having electrodes 246 and 248 with a length of 1 cm as measured along channel 245, and wherein the pressures 262 and 282 are configured to generate a flow rate of 1 cm/s along channel 245, the AC signal may be about 1 Hz. More generally, the frequency of the AC signal may be adjusted to allow a portion of or the entire sample volume to be exposed to pulsed electric fields. While the description relates to a system having a single pair of electrodes 246 and 248 along the channel 245, more pairs of electrodes may be used with small adjustments to the embodiments described herein.

The application of pulsed electric fields using electrodes 246 and 248 may also be performed intermittently, such as in coordination with the pumps generating flows 264 and 284. To that end, the flow and the electrical signals may be coordinated using a "stop-and-go" protocol. In such protocol, a short pressure pulse (e.g., a pressure pulse with a short amount of time) may be applied to generate a short displacement of the sample along channel 245. Following the short pressure pulse, a pulsed electric field may be generated from the pulse generating circuitry 102. This process, which includes the short pressure pulse and the pulsed electric field, may be repeated until the entire sample is moved between reservoirs 242 and 244.

Figure 9:
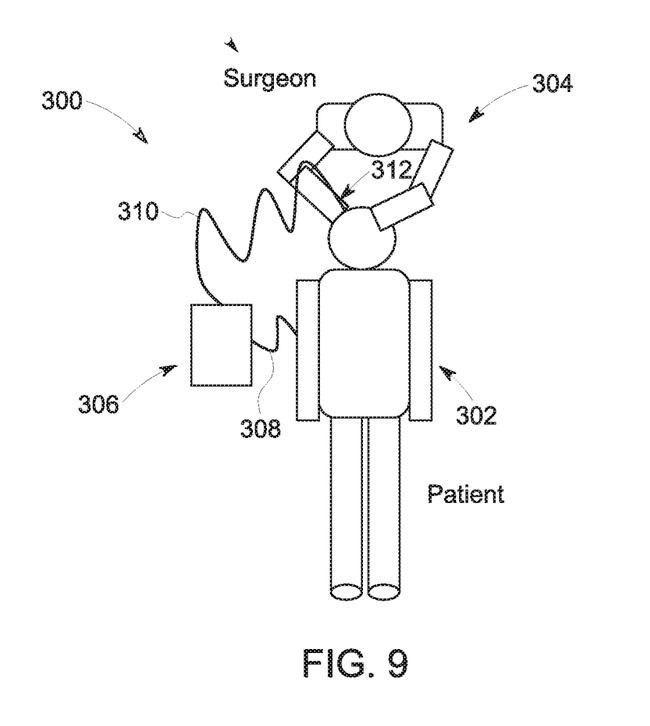
FIG. 9 is a schematic of a flow-based, on-demand platelet activation system that may be used for on-demand sample collection and activation, in accordance with an embodiment.

Flow cells may also be used for on-demand activation systems, in which the blood samples are exposed to the activating electric field pulses as they are used. Activated platelet system 300, illustrated in FIG. 9, shows an example of an on-demand system for generating activated product. In the illustration, a patient 302 is being treated by a practitioner 304 using the activated platelet system 300. The activated platelet compound may be generated using a platelet activation device 306. In the illustrated example, the platelet activation device 306 draws blood from patient 302 via a collection tube 308. The collection tube 308 may be coupled to a syringe that is placed to a vein in the patient 302. The platelet activation device 306 may expose the blood collected from patient 302 to a set of electric pulses that may activate the blood sample, as further detailed with respect to FIG. 11. The activated sample may then be applied to the patient 302 via the application tube 310.

In order to obtain on-demand functionality, the platelet activation device 306 may be configured to coordinate the pressure and the electrical signals to facilitate coordination between the product flow in application tube 310, and activation of platelets using the pulsed electric fields. During the application process, the practitioner may use an input method to request an adjustment (e.g., an increase, a decrease, a stop, a pause, a resume, a quick increase, a slow increase, a quick stop, a slow stop, etc.) in the flow of activated platelet compound in an input device 312 (e.g., a nozzle at the end of the application tube 310, a pedal of the activated platelet system, or some other input device) disposed at the end of application tube 310, or some other input device. The input device 312 may be used to apply the activated platelet product to the patient 302. In an embodiment, the input device 312 may have a trigger, or some other input mechanism, that may be used by the practitioner 304 to request an adjustment in the flow of activated product for therapy from platelet activation device 306. In another embodiment, the platelet activation device 306 may be operationally coupled to a pedal that may be used by the practitioner 304 to request the adjustment in the flow of activated product at input device 312. To that end, the trigger or the pedal may be communicatively coupled to a processor that controls parameters such as the pressure and the pulsed electric fields to adjust the flow, as described above. When the platelet activation device 306 receives the request to adjust the flow at the input device 312, the platelet activation device 306 may generate more activated product on-demand and adjust the flow of the activated product through application tube 310. This functionality is further detailed in FIG. 11.

In certain therapies, the sample may be pre-processed prior to the pulsed electric field activation. The activated platelet treatment system 320, illustrated in FIG. 10, includes a platelet activation device 322 that may be coupled to a pre-processing device 324. An example of a pre-processing system includes an automated centrifuge system that may be used to generate PRP product from raw blood product, for example. The pre-processing device 324 may have an internal receptacle 325 that may contain the pre-processed product. A collection tube 326 may be used to couple the internal receptacle 325 to the platelet activation device 322. The platelet activation device 322 may expose the pre-processed product drawn from the pre-processing device 324 to one or more electric pulse sequences that activate platelets in the pre-processed product, as further detailed in the discussion of FIG. 11. The activated platelet product may then be applied to the patient 302 via the application tube 310. The activated platelet product may be applied by an input device 312 coupled to the application tube 310, as discussed above.

Figure 10:
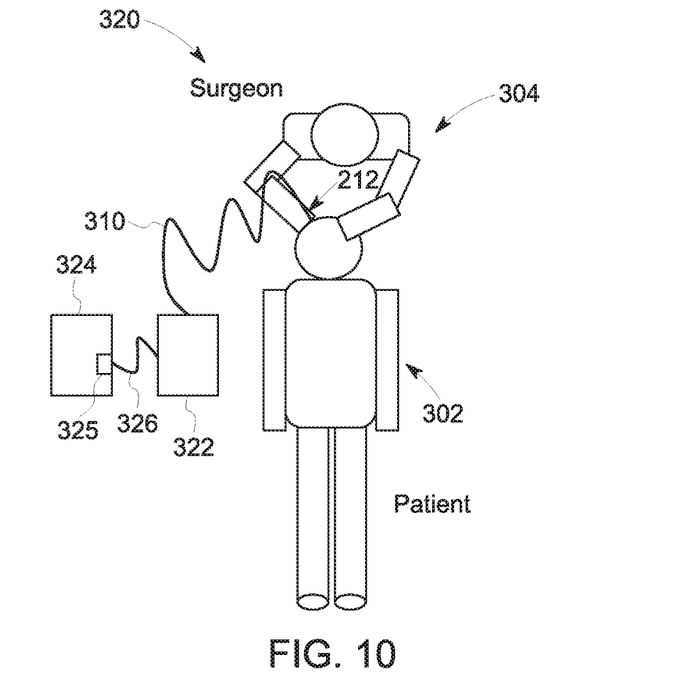
FIG. 10 is a schematic of a flow-based, on-demand platelet activation system that may be used for on-demand sample pre-processing and activation, in accordance with an embodiment.

The platelet activation device 322 of FIG. 10 may have an on-demand functionality. The platelet activation device 322 may be communicatively coupled to a pedal accessible to the practitioner 304, to a trigger in input device 312, or to some other input device. The input device may be used by the practitioner to request an adjustment to the flow at the input device 312. When the platelet activation device 322 receives the request to adjust the flow at the input device 312, the platelet activation device 322 may adjust the production. For example, if the platelet activation device 322 receives a request to increase the flow, the platelet activation device 322 may generate more activated product on-demand, and increase the flow through application tube 310, as detailed above.

Figure 11:
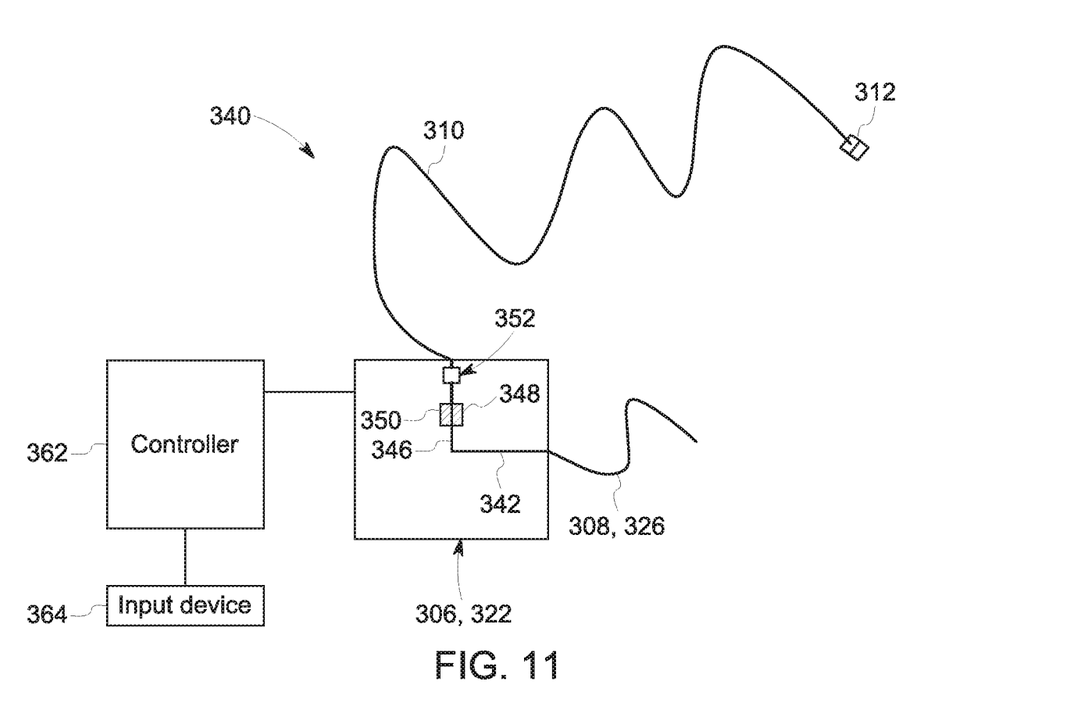
FIG. 11 is a schematic of a flow-based sample loader that may be used in on-demand platelet activation systems, in accordance with an embodiment.

FIG. 11 shows a schematic diagram 340 of an on-demand flow cell 342. The on-demand flow cell 342 may be used in platelet activation devices, such as platelet activation devices 306 of FIG. 9 and 322 of FIG. 10. The on-demand flow cell 342 may have an internal channel 346 that receives a sample from a collection tube, for example, the collection tube 308 of FIG. 9 or the collection tube 326 of FIG. 10. The internal channel 346 may have a pair of electrodes 348 and 350, which may be electrically coupled to a pulse generating circuitry. Portions of the electrodes 348 and 350 may form a portion of the internal surface of the internal channel 346. On-demand flow cell 342 may further include a fluidic pump 352. Fluidic pump 352 may be a peristaltic pump and/or a pressure pump that induces a flow along the internal channel and may push a liquid from internal channel 346 into application tube 310. As illustrated in FIGS. 9 and 10, the application tube 310 may be coupled to an input device 312, which may be used to apply the activated platelet product to the patient 302. The platelet activation device (e.g., platelet activation device 306, platelet activation device 322) may also be coupled to a controller 362, which in its turn, may receive instructions from an input device 364 operationally coupled to the controller 362. Examples of input devices include a pedal or a trigger in input device 312 or any controlling mechanism that regulates or blocks the flow to the nozzle/applicator/distributor, as discussed above.

The system illustrated in diagram 340 may operate in an on-demand manner, as discussed above. To that end, a practitioner may interact with the input device 364 to request a flow of activated platelet product at the input device 312. The controller 362, in response to the command from input device 364, may operate pulse generating circuitry (not shown) coupled to electrodes 348 and 350 to cause activation of the sample as the sample flows along the internal channel 346. Moreover, also in response to the command from input device 364, the controller 362 may operate the pressure pump 352 to push fluid from the collection tube (e.g., collection tube 308, collection tube 326) into the application tube 310. The action of the pressure pump 352 and the pulse generating circuitry may be coordinated in a similar manner as the one discussed with respect to the flow cell 241 illustrated in FIG. 7. It should be noted that pressure pump 352 may include valves to reduce the formation of bubble or similar gas accumulation that may interfere with the treatment at the input device 312. To that end, pressure pump 352 may include a valve that may allow release of accumulated air in the internal channel 346.

Technical effects of the invention include methods and systems that allow the automatic activation of large volumes (e.g., more than 1 ml) of platelets in blood and PRP samples. The embodiments describe herein may be used to obtain a faster generation of the activated platelet products in a sterile, automatic manner, with or without the use of platelet activating compounds. The use of cartridge-based systems may facilitate the production of platelet activating compounds at a large volume in a reliable manner. The use of flow-based systems may reduce the complexity of the power sources by allowing the use of reduced electrode gaps. More-over, flow-based systems discussed herein may be adapted to allow "on-demand" activation of platelet products, which may increase the efficacy of the treatment by reducing the delay between generation of the activated product and its use for treatment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An electric pulse generation system comprising:
   a sample loader comprising a cartridge rail and a pair of sample loader electrodes adjacent to the cartridge rail, wherein the cartridge rail is configured to receive a cuvette cartridge that comprises a plurality of cuvettes, and wherein each cuvette of the cuvette cartridge comprises a respective pair of electrodes;
   a motor configured to move the cuvette cartridge along the cartridge rail using a mechanical lever that contacts the cuvette cartridge;
   a pulse generating circuitry configured to generate an electrical pulse between the pair of sample loader electrodes; and
   a controller communicatively coupled to the motor and the pulse generating circuitry, and configured to:
     cause the motor to move the cuvette cartridge to a first position, wherein, in the first position, a respective pair of electrodes of a first cuvette of the plurality of cuvettes is electrically coupled and physically coupled to the pair of sample loader electrodes;
     cause the pulse generating circuitry to generate an electrical pulse between the pair of electrodes of the sample loader to cause a pulsed electric field in the first cuvette; and
     cause the motor to move the cuvette cartridge from the first position to a second position, wherein, in the second position, a respective pair of electrodes of a second cuvette of the plurality of cuvettes is electrically coupled and physically coupled to the pair of electrodes of the sample loader.

2. The electric pulse generation system of claim 1, wherein the mechanical lever comprises a screw lever.

3. The electric pulse generation system of claim 1, wherein the cartridge rail comprises a plurality of mechanical stops, and wherein each mechanical stop is associated with a position of a plurality of positions.

4. The electric pulse generation system of claim 1, wherein the cartridge rail comprises a linear cartridge rail.

5. The electric pulse generation system of claim 1, wherein the cartridge rail comprises a circular cartridge rail.

6. The electric pulse generation system of claim 1, wherein the controller comprises a memory that comprises a first protocol associated with an activation of platelet in a platelet rich plasma sample.

7. The electric pulse generation system of claim 6, wherein the memory comprises a second protocol associated with an activation of platelet in a blood sample.

8. The electric pulse generation system of claim 1, comprising the cuvette cartridge, wherein the cuvette cartridge comprises an insertable frame structure to receive the cuvettes.

9. The electric pulse generation system of claim 1, comprising the cuvette cartridge, wherein the cuvette cartridge comprises a monolithic structure that includes the plurality of cuvettes.

\* \* \* \* \*